(12) United States Patent
Meron et al.

(10) Patent No.: US 10,244,980 B2
(45) Date of Patent: *Apr. 2, 2019

(54) LARGE INTESTINE CONTENTS' DIAGNOSIS AND ACOUSTIC CHARACTERIZATION

(71) Applicant: HYGIEACARE, INC., Austin, TX (US)

(72) Inventors: Gavriel David Meron, Petah Tikva (IL); Mordechai Yehuda Frisch, Moreshet (IL)

(73) Assignee: HYGIEACARE, INC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,293

(22) PCT Filed: Jun. 14, 2016

(86) PCT No.: PCT/IL2016/050620
§ 371 (c)(1),
(2) Date: Apr. 23, 2017

(87) PCT Pub. No.: WO2017/033176
PCT Pub. Date: Mar. 2, 2017

(65) Prior Publication Data
US 2017/0367642 A1 Dec. 28, 2017

Related U.S. Application Data (63) Continuation-in-part of application No. 15/138,594, filed on Apr. 26, 2016, now Pat. No. 9,775,865.
(Continued)

(51) Int. Cl.
*A61B 5/00* (2006.01)
*A61B 7/00* (2006.01)
(Continued)

(52) U.S. Cl.
CPC .............. *A61B 5/4255* (2013.01); *A61B 5/42* (2013.01); *A61B 5/6823* (2013.01); *A61B 5/702* (2013.01);
(Continued)

(58) Field of Classification Search
CPC ............................. A61B 5/4255; A61B 7/008
See application file for complete search history.

(56) References Cited

U.S. PATENT DOCUMENTS 4,190,059 A 2/1980 Holt
4,682,979 A 7/1987 Girouard
(Continued)

FOREIGN PATENT DOCUMENTS

WO WO 2002/080775 10/2002
WO WO 2015/029039 3/2015

OTHER PUBLICATIONS

International Search Report of PCT Application No. PCT/IL16/50620 dated Dec. 20, 2016.
(Continued)

*Primary Examiner* — Rene Towa
*Assistant Examiner* — H. Q. Nguyen
(74) *Attorney, Agent, or Firm* — Pearl Cohen Zedek Latzer Baratz LLP (57) ABSTRACT

Systems, kits and methods are provided, which analyze the large intestine content and utilize acoustic signals detected during delivery of water into the large intestine and drained large intestine contents to derive large intestine characteristics such as microbiotal analysis. Systems may include a water delivery unit including a water supply and a nozzle connected thereto, configured to introduce water controllably into a patient's large intestine, and an analysis unit that provides information about the drained contents using optical examination or biological assays. The information may
(Continued)

be related to acoustic analysis of signals from acoustic sensors that are attachable to a patient's abdomen. A variety of sensor configurations, positioning options, analysis strategies and large intestine characteristics are presented.

8 Claims, 10 Drawing Sheets

Related U.S. Application Data (60) Provisional application No. 62/208,995, filed on Aug. 24, 2015, provisional application No. 62/289,944, filed on Feb. 2, 2016.

(51) Int. Cl.
    *A61K 35/37* (2015.01)
    *C12Q 1/04* (2006.01)
    *A61M 3/02* (2006.01)
    *A61K 35/00* (2006.01)

(52) U.S. Cl.
    CPC ............... *A61B 7/00* (2013.01); *A61B 7/008* (2013.01); *A61K 35/37* (2013.01); *A61M 3/0204* (2014.02); *A61M 3/0275* (2013.01); *C12Q 1/04* (2013.01); *A61B 2505/05* (2013.01); *A61B 2562/0204* (2013.01); *A61K 2035/11* (2013.01); *A61M 2205/3375* (2013.01); *A61M 2210/1064* (2013.01)

(56) References Cited

U.S. PATENT DOCUMENTS

| | | |
|---|---|---|
| 4,893,634 A | 1/1990 | Kulik |
| 5,190,519 A | 3/1993 | Mead et al. |
| 5,788,650 A | 8/1998 | Dotolo |
| 6,228,040 B1 | 5/2001 | Craine |
| 9,775,865 B2 | 10/2017 | Meron |
| 2003/0153847 A1 | 8/2003 | Sandler et al. |
| 2005/0119628 A1 | 6/2005 | Sant |
| 2006/0100595 A1 | 5/2006 | Von Dyck et al. |
| 2010/0172839 A1 | 7/2010 | Walker |
| 2013/0035610 A1 | 2/2013 | Cromwell |
| 2013/0085442 A1 | 4/2013 | Shtul et al. |
| 2013/0195804 A1 | 8/2013 | Borody |
| 2014/0323802 A1 | 10/2014 | Lloyd |
| 2014/0343451 A1 | 11/2014 | Pannell et al. |
| 2017/0367642 A1 | 12/2017 | Meron |
| 2018/0110810 A1 | 4/2018 | Sadowsky |

OTHER PUBLICATIONS

Office Action of U.S. Appl. No. 15/138,594 dated Mar. 13, 2017.
Seekatz et al., "Recovery of the Gut Microbiome Following Fecal Microbiota Transplantation", MBio 5(3):1-9, May/Jun. 2014.
Das, A et al; Rectal Infusion Based Colon Cleansing Preparation for Colonoscopy is a Dominantly Cost-Effective Strategy Compared to Standard Oral Preparation; Gastrointestinal Endoscopy 85(5S)Sa; 1732; 2017.
Office Action dated Dec. 3, 2018 for U.S. Appl. No. 15/688,877.

LARGE INTESTINE CONTENTS' DIAGNOSIS AND ACOUSTIC CHARACTERIZATION

CROSS-REFERENCE TO RELATED APPLICATIONS

This application is a National Phase Application of PCT International Application No. PCT/IL2016/050620, International Filing Date Jun. 14, 2016, which is a continuation of U.S. patent application Ser. No. 15/138,594, filed Apr. 26, 2016; PCT International Application No. PCT/IL2016/050620 further claims the benefit of U.S. Provisional Patent Applications Nos. 62/289,944, filed Feb. 2, 2016, and 62/208,995, filed Aug. 24, 2015, all of which are hereby incorporated by reference.

BACKGROUND

Technical Field

The present invention relates to the field of gastroenterological systems, and more particularly, to large intestine contents and acoustic characterization.

Discussion of Related Art

Colonoscopy procedures, carried out routinely on a large number of patients, require a prior cleansing of the large intestine, which may be carried out by various means.

SUMMARY OF THE INVENTION

The following summary does not necessarily identify key elements nor limit the scope of the invention, but merely serves as an introduction to the following description.

One embodiment of the present invention provides a method comprising introducing water controllably into a patient's large intestine, draining, by gravity, the introduced water with contents of the patient's large intestine, relating at least two portions of the drained contents with at least two sections of the large intestine, and deriving microbiome characteristics of the at least two sections of the large intestine by analyzing the corresponding at least two portions of the drained contents.

One embodiment of the present invention provides a system including a water delivery unit including a water supply and a nozzle connected thereto, configured to introduce water controllably into a patient's large intestine (typically a human patient), a plurality of acoustic sensors that are attachable to a patient's abdomen, and a processing unit connected to the acoustic sensors and configured to calculate or derive large intestine characteristics by analyzing acoustic signals received from the acoustic sensors, which are associated with the water introduction.

These, additional, and/or other aspects and/or advantages of embodiments the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION

Prior to the detailed description being set forth, it may be helpful to set forth definitions of certain terms that will be used hereinafter.

The term "large intestine characteristics" as used in this application refers to any feature that may be used to relate to the large intestine, such as its shape, length, diameter, position in the abdomen, any related structures, such as appendages and pouches, the large intestine may have, any changes in the form of the large intestine, features of the large intestine wall and its muscular activity, as well as features that are related to measured acoustic signals, such as signal levels, signal frequencies, temporal and/or spatial distribution of the signals and relation of the signals to any external or internal event such as introduction of water into the large intestine and the cleansing of the large intestine. The term "large bowel" is used interchangeably with the term "large intestine".

The term "microbiota transplant" or "MT" as used in this application refers to any introduced sample of intestinal bacteria such as fecal transplants (fecal microbiota transplants—FMT) from autologous (self) sources or from donors, as well as any probiotic infusions.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units may be at least partially implemented by a computer processor.

Systems, kits and methods are provided, which analyze the large intestine content and may utilize acoustic signals detected during delivery of water into the large intestine and drained large intestine contents to derive large intestine characteristics. Systems may include a water delivery unit including a water supply and a nozzle connected thereto, configured to introduce water controllably into a patient's large intestine, and an analysis unit that provides information about the drained contents using optical examination or biological assays. The information may be related to acoustic analysis of signals from acoustic sensors that are attachable to a patient's abdomen. A variety of sensor configurations, positioning options, analysis strategies and large intestine characteristics are presented.

Advantageously, as the gut microbiome is increasingly reported to relate to a variety of medical conditions (e.g., risk for cancer, inflammatory bowel disease (IBD), obesity, nonalcoholic fatty liver disease, arterial condition, allergies and asthma, "reset" dysbiosis, such as caused by dietary changes, antibiotics, apnea, therapies, diseases, jetlag etc.), the ability to diagnose and transplant the microbiome is expected to provide substantial benefits in many fields of medicine.

In certain embodiments, the systems, kits and methods may be integrated within a system or a procedure of large intestine cleansing prior to colonoscopy, to provide additional information in form of the large intestine characteristics to the practitioner of the upcoming colonoscopy procedure.

Figure 1:
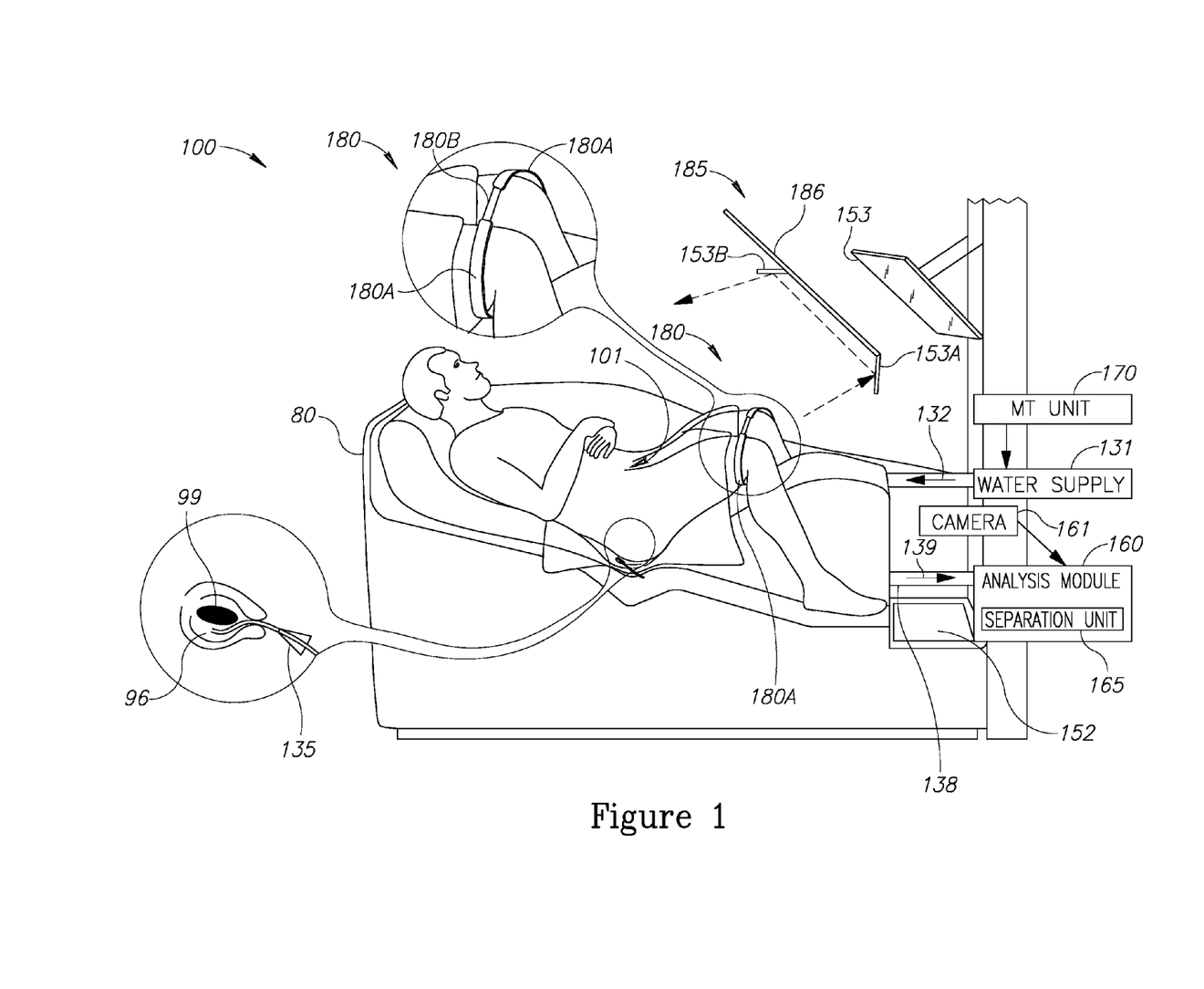
FIG. 1 is a high-level schematic illustrations of a large bowel cleansing system, according to some embodiments of the invention.

FIG. 1 is a high level schematic illustration of a large bowel cleansing system 100, according to some embodiments of the invention. Embodiments of large bowel cleansing system 100 may be integrated with embodiments of kit 101 for acoustic sensing as described below.

System 100 may include water delivery unit 130 (also see FIG. 2A below) including water supply 131 and nozzle 135 connected thereto, configured to introduce water controllably into the patient's large intestine, drainage 151 configured to drain, by gravity, the introduced water with contents of the patient's large intestine (denoted by numeral 139), and analysis module 160 configured to determine a large intestine cleanliness level according to drained contents 139 of the patient's large intestine. Analysis module 160 may be further configured to derive patient diagnostics by analyzing drained contents 139 of the patient's large intestine. For example, the analyzing may be carried out using a biological assay of drained contents 139, such as an application of cancer markers thereto. Advantageously, the analysis may be carried out using at least most of drained contents 139 or all of drained contents 139, thus providing a sample having a large volume that may enable efficient and sensitive diagnosis.

In certain embodiments, the drained large intestine's contents may be separated after its original location in the large intestine, e.g., contents of the left colon, the central colon and the right colon may be separated from each other and be characterized independently (physically, optically, chemically and/or biologically). Specific sections of the large intestine may be separated from the rest of the large intestine's content, according to specified definitions that may relate to the patient's possible medical conditions. A sequence of sections of the large intestine may be diagnosed independently, both in respect to contents as well as acoustically. The acoustic measurements may be used as indicators for the splitting of the large intestine into sections and/or may provide additional data for the analysis of the large intestine's contents from each section. The spatial information concerning the contents of the large intestine may be utilize to provide more effective medical diagnosis, as certain conditions may be location-specific, and isolating the contents from a specific section of the large intestine may provide more concentrated samples for analysis than the whole bowel contents. The possibility provided by the system to register the position of each portion of the contents opens up a new dimension in the ability to pinpoint the origins of various large intestine medical conditions (it is known, for example, that certain conditions originate from very specific locations in the large intestine, and that the microbiota may vary significantly along the large intestine).

In certain embodiments, drained contents 139 may flow via a transparent drainage pipe 138 as part of drainage 151 and the analyzing may be carried out optically through transparent drainage pipe 138. For example, a light source 152 may be located next to the transparent drainage pipe and analysis module 160 may employ optical analysis methods using camera(s) 161 and image processing software, possibly as part of optical inspection unit 150 (illustrated in FIG. 2A). Camera 161 may be used to record effluent 139 seen in viewing tube 138 for monitoring progress of cleanliness of the bowel from a control center external to the room where the patient is located, and an analytical tool in analysis module 160 may be configured to perform analysis of pathological indicators e.g., excretion of red blood, black stool, indicators of diverticula (such as corresponding pellets of stool). Image processing may be carried out locally or by a remote service and diagnosis of the images may be carried out automatically (e.g., by the analytical tool), manually, e.g., by a local or remote expert or by a combination thereof. The analytical tool may comprise algorithms configured to generate corresponding alerts once finding suggest any type of abnormality.

Analysis module 160 may be further configured to relate at least two portions of the drained contents with at least two sections of the large intestine. The relation may be carried out e.g., according to the time of drainage of the portions, according to characteristics of the drained content (e.g., consistence, shape, color, etc. related to diagnosed conditions in the large intestine sections), according to acoustic measurements of the large intestine section and the drainage and/or according to modifications in the pressure of the introduced water and drained contents, which may be related to positional information along the large intestine.

Analysis module 160 may be further configured to derive microbiome characteristics of the at least two sections of the large intestine by analyzing the corresponding at least two portions of the drained contents. For example, a diversity, an abundance, and chemical and/or genetic characteristics of the microbiome may be derived from analyzing different portions of the contents. The microbiome characterization may be used to reinstate the original microbiome after a treatment, or be modified under spatial analysis of a present and a specified microbiome. In certain embodiments, the drained contents may be used to provide a FMT for transplantation after a treatment as an auto-FMT. Any type of microbiotic infusion may be used as microbiota transplant (MT) to enhance or replace the characterized microbiome, at least on one section of the large intestine. Advantageously, system 100 enables use of most or all of the drained contents for characterizing the microbiome of the patient, thus providing an exhaustive and reliable analysis.

For example, the microbiotic diagnosis and transplant may be used to diagnose and treat *Clostridium difficile* (C. Diff) infections. The combined treatment of cleansing the large intestine and transplanting a MT may be combined using system 100, thus becoming cleansing and transplantation system 100. Moreover, system 100 may be used to provide a healthy donor-based stool bank, which stores large intestine contents from healthy subjects (being prepared from colonoscopy examinations by cleansing system 100) that may be used for research and treatment. Moreover, donors to the stool bank may utilize the stored probes for microbiome rehabilitation after deterioration, thus treating "reset" dysbiosis, such as caused by dietary changes, antibiotics, apnea, therapies, diseases, jetlag, by autologous FMT. The whole stool sampling may be used to overcome the inherent patchiness of the microbiome and patchiness patterns may be analyzed using the accumulating contents from many patients.

Certain embodiments comprise using system 100 to drain and to store a plurality of the drained contents' samples from a plurality of the patients, in association with the derived microbiome characteristics of the drained contents samples. Moreover, system 100 may be utilized to establish a stool bank for storing and providing drained contents' samples. Certain embodiments comprise a stool bank with the plurality of drained large intestine contents' samples from the plurality of patients, associated with derived microbiome characteristics of the drained large intestine contents samples, wherein the drained large intestine contents' samples are drained by gravity after controllable water introduction into the patients' large intestines. The samples may be used in different ways, e.g., for infusion (transplantation) of certain pre-screened stool samples and/or of related microbiome infusions; for administering of specific bacteria, probiotics, or antibiotics related to the derived microbiome characteristics; for infusion (transplantation) of autologous samples; for prescribing food additives, food supplements, medications and/or therapies related to the derived microbiome characteristics. Any of the above may be related to specific patients and/or to specific patient groups.

Returning to FIG. 1, in certain embodiments, a mirror 153 above transparent drainage pipe 138 may reflect drained contents 139 to a camera and an image processing unit, and/or to a staff person to determine the consistency of drained contents 139, specific diagnostic appearances (e.g., color, objects etc.) and eventually the cleanliness level of the patient's large intestine by noting the amount of drained content 139 flowing through drainage 151. It is noted that mirror 153 may also be used by the patient and/or by a staff member to simplify the process of inserting nozzle 135 into patient's anus 96. Alternatively or complementarily, a utensil 185 including two mirrors 153A, 153B mounted on a handle 186 may be configured to enable visualization of the nozzle insertion by the patient and/or by the physician. Utensil 185 may be designed or be configurable to enable easy self-insertion of nozzle 135 into anus 96 by the patient, or simplify the insertion procedure when carried out by a physician or other medical personnel.

System 100 may include a support 180 configured to support the patient's legs to help the patient maintain an appropriate posture during the procedure. For example, support 180 may have two interconnected hooks 180A, one for supporting each leg or knee. Hooks 180A may be interconnected by any connecting member 180B such as a flexible or rigid strap or bar, a band etc. Support 180 may be configured to anchor the legs of the patient on hydrocolonic preparation system 100, allowing the legs to fall sideways while supporting them against each other (the force applied by each leg on respective hook 180A are balanced and maintained by connecting member 180B) to maintain a required posture conveniently, as water flows through the nozzle into the rectum. Support 180 may be configured to allow the patient to sit comfortably in the required position for an extended period of time as may be required by the procedure.

In certain embodiments, analysis module 160 may be further configured to derive large intestine characteristics by analyzing parameters of drained water and contents 139. For example, an exceptionally large amount of contents 139 may signify a large volume of large intestine, or contents 139 with specific features may be used to indicate specific large intestine features (e.g., small hard round clumps may signify large intestine diverticula). Certain large intestine characteristics may be corroborated by deriving them from both the acoustic signals and the contents analysis.

In certain embodiments, system 100 may further include a MT unit 170 configured to transplant a microbiota transplant (MT) such as a fecal microbiota transplant (FMT) into the patient's large intestine after a predetermined cleanliness level thereof is determined MT transplantation may be carried out e.g., via water supply, before or after cleansing and/or colonoscopy.

In certain embodiments, water delivery unit 130 may be further configured to modify a pressure of introduced water 132 and analysis module 160 may be further configured to measure a pressure of drained water and contents 139, and derive large intestine characteristics by correlating the measured drainage pressure with the pressure of introduced water according to a specified model. The reaction of the large intestine to different pressures may indicate certain characteristics thereof, such as peristaltic parameters of the large intestine and possibly certain anomalies. Measuring the difference in pressure between the water flowing into the anus (132) and the effluent flowing out of the anus (139) may be used to provide new information regarding the effectiveness of the peristaltic waves created by the muscles of the colon. Acoustic signals relating to the introduction of pressurized water may also be analyzed to derive additional information about the large intestine, so that the analysis of the acoustic signals and the analysis of the contents of the large intestine may be combined synergistically.

Certain embodiments may include any combination of acoustic signal sensing and large intestine content analysis. For example, system 100 may include water delivery unit 130 including water supply 131 and nozzle 135 connected thereto, configured to introduce water controllably into the patient's large intestine, drainage 151 configured to drain, by gravity, the introduced water with contents of the patient's large intestine, acoustic sensor(s) 110 that are attachable to the patient's abdomen, and processing unit 120, possibly incorporating analysis unit 160, configured to determine a large intestine cleanliness level according to drained contents 139 of the patient's large intestine as well as to derive large intestine characteristics by analyzing and correlating acoustic signals received from acoustic sensors 110, to which processing unit 120 is connected, with parameters of the drained water and contents.

Figure 2A:
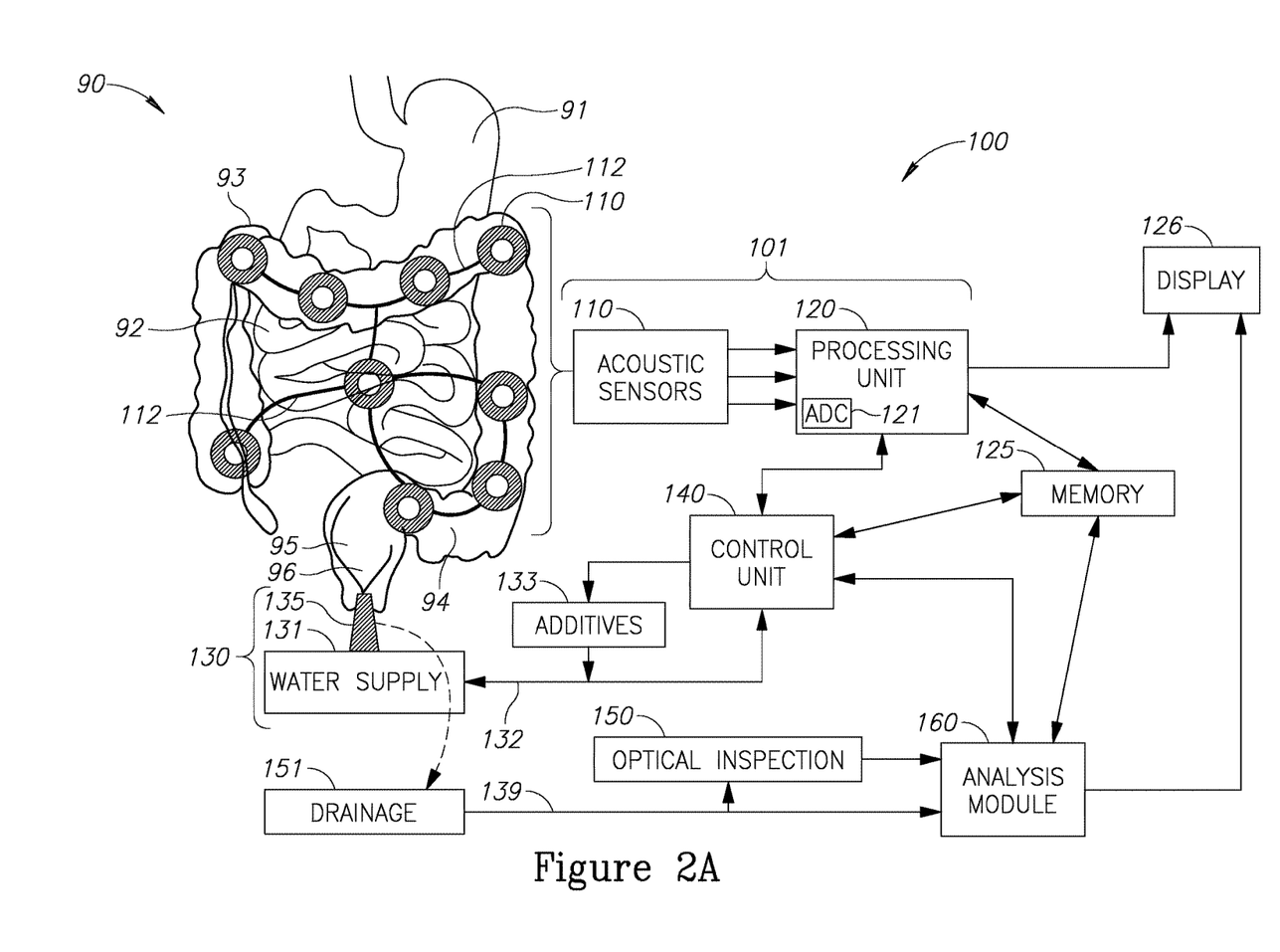
FIGS. 2A-2C are high-level schematic illustrations of a system, according to some embodiments of the invention.
Figure 2B:
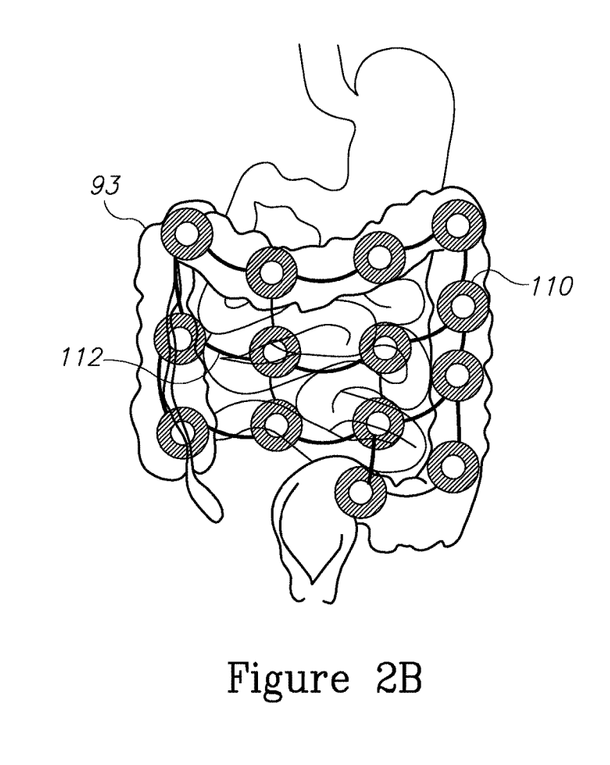
Figure 2C:
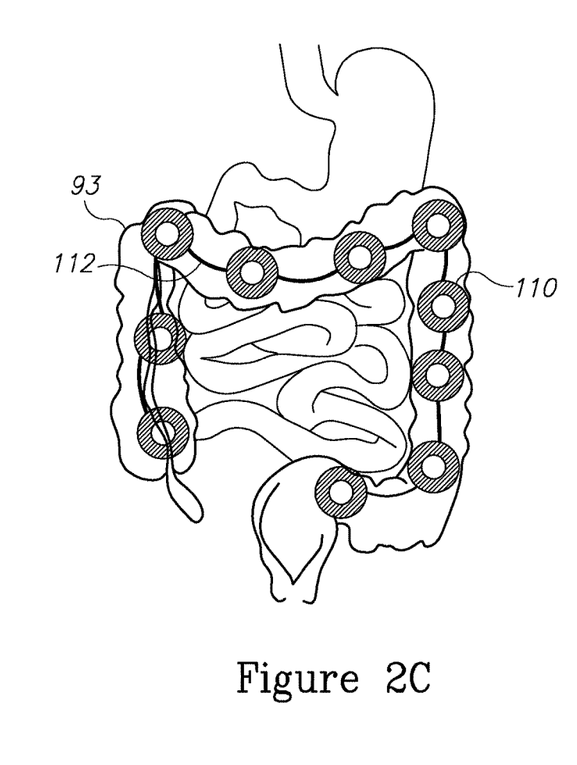

FIGS. 2A-2C are high level schematic illustrations of a system 100, according to some embodiments of the invention. It is noted that elements of system 100 from FIGS. 1 and 2A may be combined to various embodiments of system 100. System 100 may be used to calculate or derive information about a patient's large intestine by processing acoustic signals received by sensors placed on the patient's abdomen. The information may be provided to physician, e.g., as preparation for colonoscopy procedures. It is noted that the illustrated elements of the patient's digestive tract 90, namely stomach 91, small intestine 92, large intestine 93, sigmoid colon 94 (being the last part of large intestine 93), rectum 95 and anus 96 are shown schematically, in a non-limiting manner. FIG. 2A schematically illustrates system 100 while FIGS. 2B and 2C schematically illustrate sensor configurations, according to some embodiments of the invention. System 100 may be configured to cleanse the patient's large intestine, e.g., as a preparation for a colonoscopy procedure.

The inventors have found out that the acoustic signals, e.g., ones generated during the cleansing of the large intestine, may be used to derive significant information about the large intestine, such as indications whether the structure and position of the large intestine are normal or abnormal, simple or complex, and/or adequate or not for performing colonoscopy (abnormalities and complexity may be of different kinds); and various large intestine characteristics such as geometric parameters thereof and flow characteristics therethrough. The derivation of the large intestine characteristics may be carried out experimentally, by relating measured acoustic signals to known large intestine characteristics in a calibration process, utilizing theoretical or empirical models describing flow properties through the large intestine and by comparing acoustic signals from different parts of the abdomen and/or from different measurement times to derive differences that are indicative of large intestine characteristics or progress of the water flow and cleansing into the proximal large intestine (closer to the cecum and distal to the anus). As a simple example, the measurement of flow noise may be used to indicate the location and general form of the large intestine. In another example, modifying water flow through the large intestine and correlation thereof with the changing acoustic signals may be used to refine the measurement of geometrical parameters of the large intestine and furthermore provide information about flow patterns therethrough (e.g., indicate the resistance of the large intestine to flow, enable as evaluation of intestine wall thickness, relate to the peristaltic movements of the large intestine etc.). Large intestine characteristics may be measured spatially, relating to specific sections of the large intestine.

System 100 may include a water delivery unit 130 including a water supply 131 (e.g., a container with a controlled outflow valve) and a nozzle 135 connected thereto, configured to introduce water through nozzle 135 controllably (as explained below) into a patient's large intestine 93, a plurality of acoustic sensors 110 (e.g., microphones) that are attachable to a patient's abdomen, and a processing unit 120 which is connected to acoustic sensors 110 and is configured to calculate or derive large intestine characteristics by analyzing acoustic signals that are related to noise received from acoustic sensors 110, the noises resulting from movements of water, large bowel content and/or air bubbles through the large intestine, that are initiated through the water introduction. Sounds of water flow introduced into the large intestine may allow diagnosing structural features of large intestine 93 such as its shape and layout, dimensions of its various section, width along its length and presence of specific features such as pouches (diverticula), redundant loops, irregular geometrical and/or positional features etc.

In certain embodiments, acoustic sensors 110 may be configured to communicate with processing unit 120 over wires or wirelessly, the latter via transmitters attached to acoustic sensors 110 which do not have a galvanic connection to the patient's body.

System 100 may include a control unit 140 configured to control water delivery unit 130 according to instructions or control signals received from processing unit 120 which relate to the acoustic signals analysis. For example, water delivery may be stopped, increased, enhanced, made periodic or any parameters of water delivery may be modified in order, e.g., to verify or improve analysis initial findings.

Processing unit 120 may be configured to compare acoustic signals emanating from the large intestine with acoustic signals emanating from other regions, e.g., the small intestine, to identify and remove background acoustic noise. For example, one or more sensors 110 may be positioned away from large intestine 93 (see e.g., central sensor 110 in FIG. 2A or four central sensors in FIG. 2B) and their signals may be used as characterizing the background noise. Processing unit 120 may receive multiple channels from sensors 110, convert the analog audio signals into digital signals (by analog to digital converter, ADC 121) and further process the digital signals.

Processing unit 120 may be configured to compare acoustic signals (from large intestine noises) received before the water introduction with acoustic signals received after the water introduction and/or processing unit 120 may be configured to compare acoustic signals received before the introduced water reaches at least one specified region with acoustic signals received after the introduced water reaches the at least one specified region. In certain embodiments, signals received from sensors 110 positioned along large intestine 93 (see e.g., FIG. 2C and the corresponding sensors in FIGS. 2A and 2B) and sampled sequentially to track water reaching the corresponding large intestine sections positioned below sensors 110. The sequential sampling may include sampling sensors 110 according to the position along the large intensity, sampling one or more sensors 110 sequentially over a specified period of time (e.g., over the time it takes to fill and/or empty the large intestine) and/or any combination of these sampling approaches. In certain embodiments, water delivery unit 130 may be configured to introduce air bubbles of different sizes into the large intestine (e.g., air bubbles of different sizes maybe introduced simultaneously or bubbles of uniform but selectable size may be introduced at one or several times), and processing unit 120 may be configured to calculate or derive information from acoustic signals emitted due to the bubble introduction and bubble behavior in the large intestine. For example, bubble-induced noises may be used to improve the delineation of the large intestine, to derive information about the diameter of the large intestine at different portions thereof and/or to indicate pressure levels that characterize different sections of the large intestine (varying the pressure of introduced water, which is described below, may be applied to achieve this end together with the introduction of bubbles). Processing unit 120 may be configured to utilize and/or analyze any type of water-flow and air-flow modulations and the progress along the large intestine of flow noise resulting from the introduction. Sensors 110 may be placed accordingly along the nominal location of the large intestine, and/or at additional locations for reference and/or for detecting abnormalities or exceptional features in the large intestine, especially ones relating to the performance of a subsequent colonoscopy procedure (see FIGS. 3A-3D below for more details on the acoustic signal analysis).

In certain embodiments, acoustic sensors 110 may be attached along an expected position of the patient's large intestine (see e.g., FIG. 2C), additional sensors 110 may be attached at at least one location aside from or not at the expected position of the patient's large intestine (see e.g., FIGS. 2A and 2B) and/or acoustic sensors 110 may be attached at an array covering the patient's abdomen (see e.g., FIG. 2B). The positioning of sensors 110 may be optimized over a large number of patients and water delivery schemes and/or may be personalized according to each patient's specific characteristics and possibly modified in view of accumulating analysis results.

In certain embodiments, sensors 110 may be connected to a frame or framework 112 configured or adapted to an expected form of the patient's large intestine. Framework 112 may be stiff or flexible, and may allow accommodation to the shape and dimensions of the patient's abdomen. Sensors 110 may be attached to the patient's abdomen by various means such as suction, adhesion (e.g., stickers), structural conformity to the patient's abdomen and/or by the configuration of framework 112 to yield effective transfer of acoustic waves from the patient's body to sensors 110. In certain embodiments, framework 112 may be wearable, e.g., sensors 110 may be incorporated in a vest as framework 112, configured to facilitate correct positioning of sensors 110.

In certain embodiments, the water introduction may include at least one time period of continuous water introduction and at least one period of a pulsated or intermittent water introduction, and processing unit 120 may be configured to analyze acoustic signals received during the at least two periods.

In certain embodiments, the sensed acoustic signals and/or the calculated or derived large intestine characteristics may be used to derive an alert or indication concerning a consequent colonoscopy procedure and/or an indication of large intestine anomaly, exceptional features or adequacy for colonoscopy. The alert or indication may be delivered as any type of output, such as a textual indication, a visual or an auditory signal and so forth, and by any medium (e.g., a display, a speaker, a medical record etc.). In certain embodiments, the calculated or derived large intestine characteristics may include for example: an indication of large intestine anomaly, a categorization of the patient's large intestine (e.g., into medically significant classes), at least one geometric parameter of at least one region of the large intestine (e.g., length, width, position, wall thickness, etc.) and at least one parameter of water flow through the large intestine (such as throughput, speed of flow, regions which receive little or no flow, etc.).

Certain embodiments include a kit 101 (FIG. 2A) including acoustic sensors 110 that are attachable to a patient's abdomen, and processing unit 120 connected to acoustic sensors 110 and configured to derive large intestine characteristics by analyzing acoustic signals received therefrom, which are associated with water introduction to the patient's large intestine. The placing of sensors 110, configurations of processing unit 120 and derived large intestine characteristics may be similar to the one described above for system 100. Kit 101 may comprise the parts of system 100 which handle the acoustic sensing and processing, such as acoustic sensors 110 and elements of processing unit 120 and related units. Kit 101 may include placing instructions for acoustic sensors 110 and/or diagnostic flow(s) that relate processing results with the large intestine characteristics and/or with corresponding medical conditions.

In certain embodiments, system 100 may further include a drainage 151 configured to drain, by gravity, introduced water with contents of the patient's large intestine 139 and an analysis module 160 (which may be part of, integrated with or include processing unit 120) that is configured to determine a large intestine cleanliness level according to the drained contents of the patient's large intestine. Further details were provided above concerning FIG. 1. Analysis module 160 may comprise a separation unit 165 such as a mesh apparatus, configured to separate contents of the large intestine such as feces from the water in drained contents 139.

System 100 may be configured to cleanse the patient's large intestine, e.g., as a preparation for a colonoscopy procedure. Water delivery unit 130 may be further configured to introduce at least one additive 133 with introduced water 132. Additive(s) 133 selected to enhance cleansing of the patient's large intestine. For example, at least one additive 133 may include biological detergents that can be shown to be acceptable for use in large intestine cleansing procedures.

Analysis of drained material 139 may be carried out, for example optically, by an optical inspection unit 150 and/or using a biological assay, such as one including various markers, e.g., cancer markers. Processing unit 120 may be configured to determine existence of specific diseases based on analyzing biological reactions of the contents of the patients' large intestine to markers for such diseases. It is emphasized that the analysis may be carried out with respect to most or all of the large bowel contents, thus providing significant diagnostic advantages over prior art diagnosis that is based on partial sampling of the large bowel content. The biological assay may be carried out as part of system 100 or at least partially by external labs. The biological assay may be carried out in real-time, or at least partially a certain period after the contents has been drained.

Processing unit 120 and/or control unit 140 and/or analysis module 160 may be configured to carry out methods according to embodiments of the present invention by for example executing software or code (for example stored in memory 125) and/or by including dedicated circuitry.

Figure 3A:
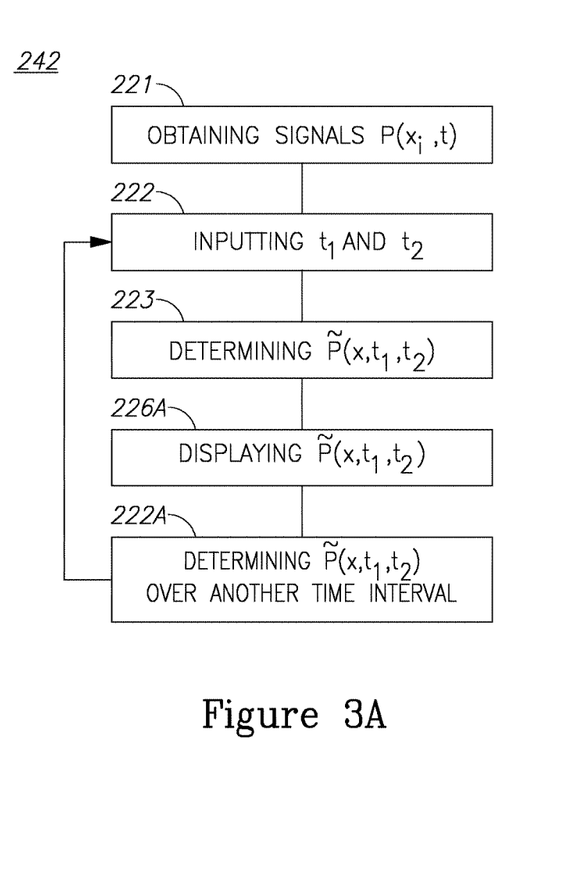
FIGS. 3A-3D are high-level schematic flowcharts and illustrations of methods of deriving large intestine characteristics from acoustic signals, according to some embodiments of the invention.
Figure 3B:
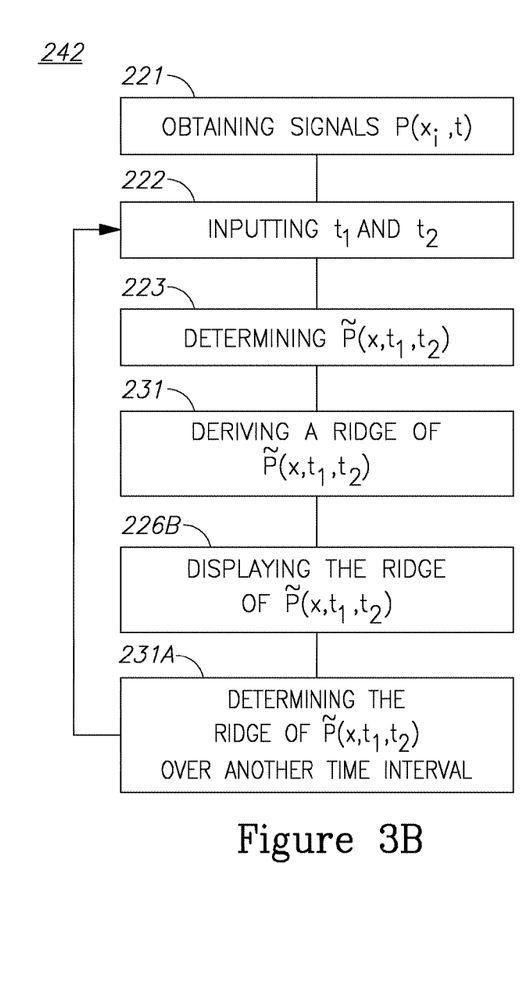
Figures 3C, 3D:
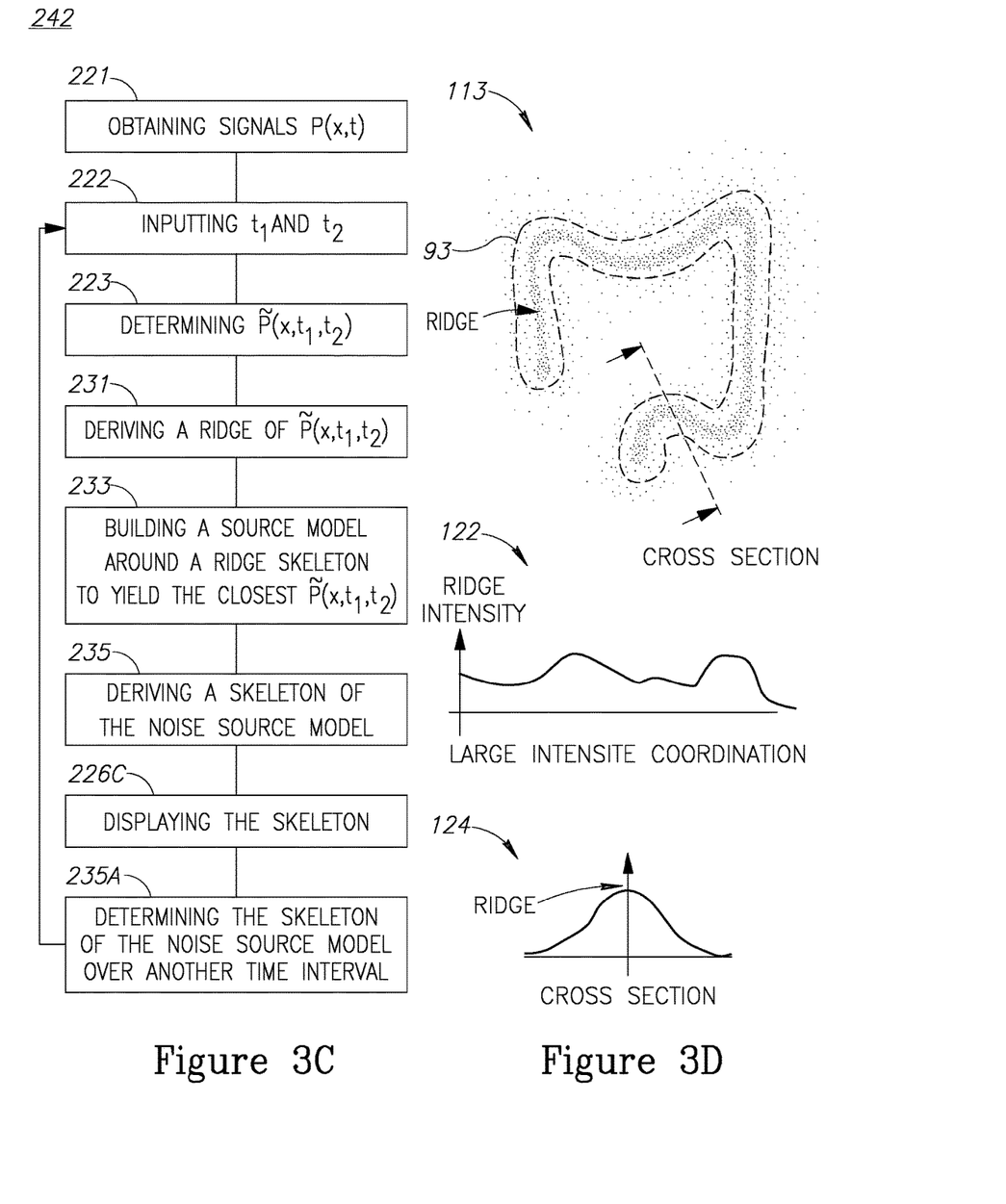

FIGS. 3A-3D are high level schematic flowcharts and illustrations of methods 242 of deriving large intestine characteristics from acoustic signals, according to some embodiments of the invention. Methods 242 may commence with acquiring or obtaining the acoustic signals (stage 221), denoted by $P(x_i, t)$–P for the signals, x, for the respective location of the $i^{th}$ sensor 110 and t for the time from the beginning of the measurements, inputting or receiving a start time $t_1$ and an end time $t_2$ (stage 222) and determining a noise pattern $\tilde{P}(x, t_1, t_2)$ (stage 223, and see FIG. 3D below). Then, FIG. 3A exemplifies an option of displaying $\tilde{P}(x, t_1, t_2)$ (stage 226A) for further visual analysis or for deriving certain alerts or indications that are based on the appearance of the noise pattern, and then enabling determining the noise pattern $\tilde{P}(x, t_1, t_2)$ for another interval $(t_1, t_2)$ (stage 222A). Alternatively or complementarily, FIG. 3B exemplifies an option of deriving a ridge of $\tilde{P}(x, t_1, t_2)$ (stage 231), the ridge representing the line of the smallest gradient of $\tilde{P}(x, t_1, t_2)$ (alternatively or complementarily, the ridge may represent a central line of the noise pattern that exhibits the highest noise values in a set of cross sections of the pattern), and then displaying the ridge of $\tilde{P}(x, t_1, t_2)$ (stage 226B) for further visual analysis or for deriving certain alerts or indications that are based on the appearance and location of the ridge and then enabling determining the ridge of the noise pattern $\tilde{P}(x, t_1, t_2)$ for another interval $(t_1, t_2)$ (stage 231A). As illustrated in FIG. 3D, a noise pattern 113 may expand beyond large intestine 93, depending on the sensitivity of sensors 110, their density and locations, the propagation of noise through the patient's abdomen and possible pre-processing algorithms applied to the sensor data. FIG. 3D illustrates schematically noise pattern 113 ($\tilde{P}$) which is centered along large intestine 93 and exhibits a central ridge, i.e., a substantially linear region exhibiting the lowest gradient (and optionally the highest noise level along the cross section) of noise pattern 113. FIG. 3D further illustrates schematically changes in noise intensity along the ridge in graph 122 and the cross section of the pattern's intensity, topping at the ridge, in graph 124. Clearly, the wider pattern 113 is, more refined algorithms are required in order to detect the ridge. Sensors 110, their positions and/or the sound processing algorithms may be adjusted to optimize the detection of a clear ridge in pattern 113. FIG. 3C exemplifies another option, of building a source model around an initial skeleton, which is a two-dimensional projection of the ridge (e.g., onto the plane of the large intestine), then constructing a tubular noise source model around the skeleton and refining skeleton to yield the closest noise pattern $\tilde{P}(x, t_1, t_2)$ that fits the measured noise map (stage 233), deriving a skeleton (as estimation of the central line of the large intestine) of the refined noise source model (stage 235), i.e., estimating the outline of the large intestine, and displaying the skeleton as an approximation to the location of the large intestine (stage 226C). The skeleton may then be determined for another interval $(t_1, t_2)$ (stage 235A), and the subsequent skeletons may be used for refinements until a final, most accurate skeleton is reached and used for display. In certain embodiments, the dimensions and layout of the large intestine may be approximated by estimating the distribution of water flow noise sources in the abdomen by means of estimating the skeleton and dimensions of the noise source model that gives rise to the measured and interpolated noise map. Comparisons of the noise source model at different times, or of developing noise source models over time (progress of water flow in the large bowel over time), or of different noise sources (with or without bubbles) or with and without water flow are possibly based on the schemes illustrated in FIGS. 3A-3C. Using the noise source model may improve the derivation of the location of the large intestine by taking into account models for noise propagation within the patient's abdomen, thus removing some of the spatial ambiguity in the acoustic signals depicted by sensors 110.

Figure 4:
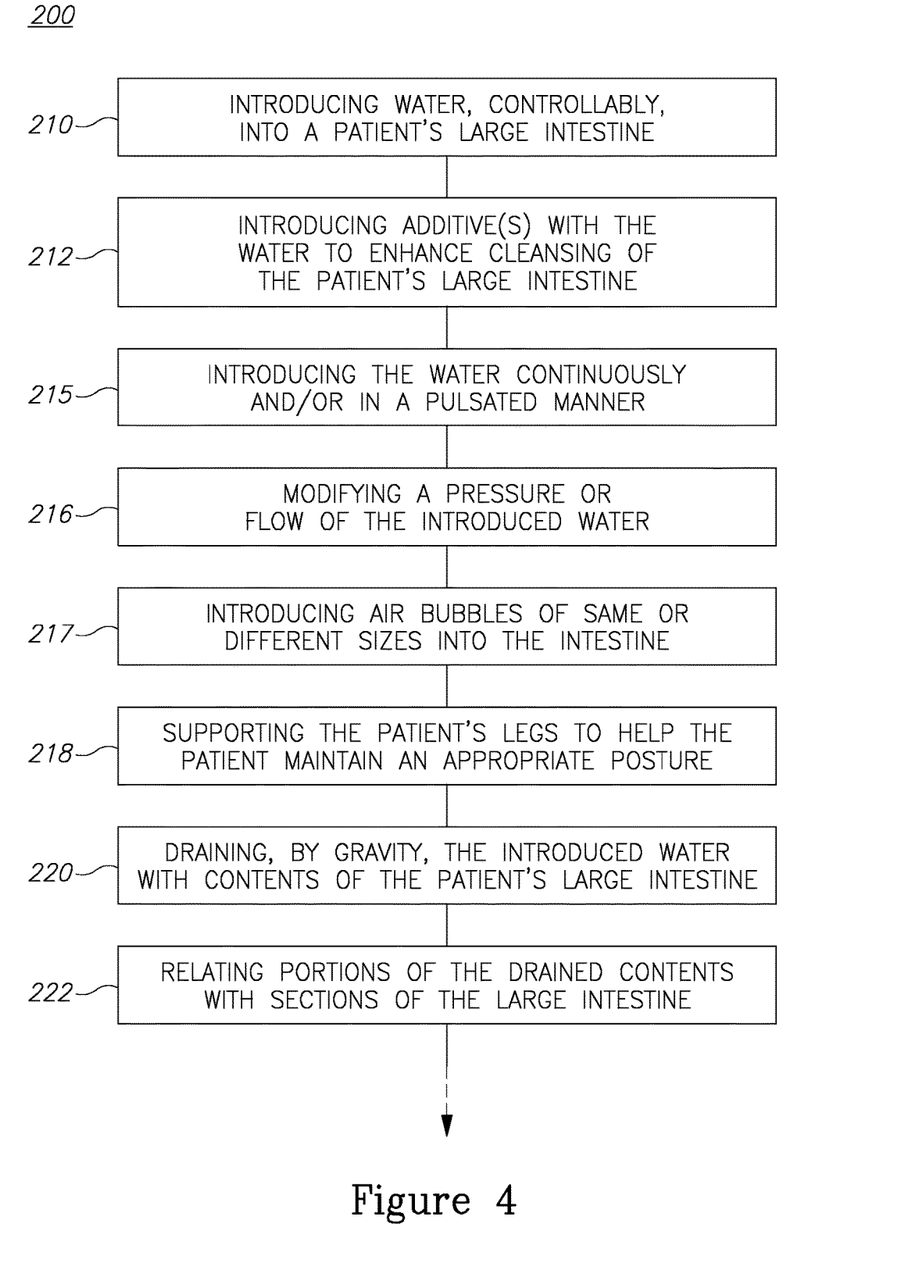
FIG. 4 is a high-level flowchart illustrating a method, according to some embodiments of the invention.

FIG. 4 is a high level flowchart illustrating a method 200, according to some embodiments of the invention. Method 200 may be carried out using system 100, kit 101 and/or equivalent devices, or other equipment. Other operations or steps may be included. Method 200 may be at least partially implemented by at least one computer processor. Certain embodiments comprise computer program products comprising a computer readable storage medium having computer readable program embodied therewith and configured to carry out of the relevant stages of method 200.

Method 200 may comprise introducing water controllably into a patient's large intestine (stage 210), draining, by gravity, the introduced water with contents of the patient's large intestine, i.e., with the large bowel contents (stage 220), relating at least two portions of the drained contents with at least two sections of the large intestine (stage 222) and deriving microbiome characteristics of the at least two sections of the large intestine by analyzing the corresponding at least two portions of the drained contents (stage 224). Method 200 may further comprise selecting a microbiota transplant (MT) such as a fecal microbiota transplant (FMT) or a microbiotic transfusion according to the derived microbiome characteristics of the at least two sections of the large intestine (stage 226) and transplanting the MT, possibly into a specified location related to the characterized section(s) of the large intestine (stage 228). The MT may comprise an autologous FMT, e.g., extracted prior to a treatment and transplanted after the treatment, or any donor FMT or artificial microbiota.

Method 200 may comprise introducing water controllably into a patient's large intestine (stage 210), sensing acoustic signals at a patient's abdomen (stage 240) and deriving large intestine characteristics by analyzing the sensed acoustic signals associated with the water introduction (stage 242). In certain embodiments, method 200 may further include introducing at least one additive with the water to enhance cleansing of the patient's large intestine (stage 212), for example, biological and/or bio-compatible detergents that can be shown to be acceptable for use for cleansing the large intestine.

Method 200 may further include identifying local maxima in the sensed noise and deriving an estimated mid-line, or ridge, therefrom (stage 244). In certain embodiments, method 200 may include modelling noise generation in the large intestine and deriving model parameters from the measured noise patterns (stage 246).

Method 200 may include controlling the water introduction according to results of the acoustic signals analysis (stage 248), e.g., to improve sensor readings, analysis and/or derivation of large intestine characteristics.

Method 200 may include for example comparing acoustic signals that are sensed before and after the water introduction (stage 250), comparing acoustic signals from different locations on the patient's abdomen (stage 255), and comparing acoustic signals that are sensed before and after the introduced water reaches at least specified one region (stage 260).

Method 200 may include introducing the water continuously and/or in a pulsated manner (stage 215) and/or introducing air bubbles of different sizes into the intestine (stage 217). Method 200 may include supporting the patient's legs to help the patient maintain an appropriate posture (stage 218), e.g., by a utensil that has two interconnected hooks, one for supporting each leg or knee. Method 200 may further include comparing acoustic signals sensed during continuous and/or pulsated water introduction and/or bubble introduction (stage 265).

Method 200 may further include deriving at least one of: an alert concerning a consequent colonoscopy procedure, an indication of a large intestine anomaly, a categorization of the patient's large intestine, geometric parameter(s) of region(s) of the large intestine and parameter(s) of water flow through the large intestine (stage 270).

In certain embodiments, method 200 may include introducing water controllably into a patient's large intestine (stage 210), draining, by gravity, the introduced water with contents of the patient's large intestine, i.e., with the large bowel contents (stage 220), and determining a large intestine cleanliness level according to the drained contents of the patient's large intestine (stage 290).

Method 200 may further include deriving patient diagnostics by analyzing the drained contents of the patient's large intestine (stage 230). For example, the analyzing may be carried out optically, e.g., through a transparent drainage pipe. Additionally or alternatively, the analyzing may be carried out using a biological assay (e.g., by application of cancer markers) of the drained contents (stage 232). In certain embodiments, most or all of the drained contents may be used for the analyzing (stage 235), improving thereby significantly the diagnostic power of the analysis with respect to prior art methods which are based on small samples of large bowel content.

Method 200 may further include deriving large intestine characteristics by analyzing parameters of the drained water and contents (stage 300). Examples for deriving large intestine characteristics include geometric measures of the large intestine (e.g., volume, length, diameter), physiological measures and anomalies of the large intestine relating to parameters of the drained contents, and so forth. The derivations of large intestine characteristics by analyzing the sensed acoustic signals associated with the water introduction (stage 242) and by analyzing parameters of the drained water and contents (stage 230) may be combined to verify findings and/or to derive compound large intestine characteristics. Moreover, the timing of the received acoustic signals may be correlated with the timing of content drainage to identify causes for specific or generic types of acoustic noise received by the sensors. These analyses may be combined to derive or enhance the derivation of temporal parameters of water and large bowel content flow through the large intestine.

In certain embodiments, method 200 may further include transplanting a microbiota transplant (MT, the term is used as a generalized term to include fecal transplants and probiotic infusions) into the patient's large intestine after a predetermined cleanliness level thereof is determined (stage 310). MT/FMT transplantation may be carried out before or after colonoscopy, or as a separate procedure. The location for FMT transplantation may be determined or evaluate according to the derived large intestine characteristics, e.g., with reference to specific structures, locations or abnormalities in the large intestine. The efficiency of MT transplantation may be enhanced by selecting a location with predefined flow parameters which are conducive to successful MT transplantation. MT transplantation may be carried out according to the derived patient diagnostics, e.g., upon detection of certain large intestine infections, and responsive thereto.

Method 200 may further comprise storing drained contents' samples from multiple patients, associated with their derived microbiome characteristics (stage 320) and establishing a stool bank for storing and providing drained contents' samples (stage 325), for auto- and/or allogenic (self and/or foreign) FMT transplantation.

In certain embodiments, method 200 may include modifying a pressure or flow of the introduced water (stage 216), measuring a pressure or flow of the drained water and contents (stage 280), and deriving large intestine characteristics by correlating the measured drainage pressure or flow with the pressure or flow of introduced water according to a specified model (stage 285). Exemplary large intestine characteristics may comprise characteristics of different sections in the large intestine, relating e.g., to a left part, to a central part and to a right part of the large intestine. The spatial characterization of the large intestine's contents may be enhanced by the acoustic spatial characterization described above. Method 200 may comprise analyzing the large intestine's contents with respect to at least one portion of the contents which correspond to a respective derived at least one section of the large intestine. The derivation of the specific section may be carried out physically, e.g. with respect to the volume of outflowing contents, or acoustically, simultaneously with the acoustic sensing described above.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram portion or portions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function(s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method comprising:
   introducing water controllably into a large intestine of a patient,
   sensing, by at least one acoustic sensor, acoustic signals at an abdomen of the patient, and
   deriving, from the sensed acoustic signals and by a data processing unit, large intestine diagnostic characteristics relating to the patient's large intestine by analyzing the sensed acoustic signals associated with the water introduction
   wherein the derived large intestine diagnostic characteristics provide gastrointestinal diagnosis of the patient.

2. The method of claim 1, further comprising controlling the water introduction according to results of the analyzing of the sensed acoustic signals.

3. The method of claim 1, further comprising comparing the sensed acoustic signals, which are sensed before and after the water introduction.

4. The method of claim 1, further comprising comparing the sensed acoustic signals, which are sensed before and after the introduced water reaches at least specified one region of the patient's large intestine.

5. The method of claim 1, wherein the derived large intestine diagnostic characteristics comprise at least one of: an indication of a large intestine anomaly, a categorization of the patient's large intestine, at least one geometric parameter of at least one region of the patient's large intestine and at least one parameter of water flow through the patient's large intestine.

6. The method of claim 1, further comprising deriving an alert concerning a consequent colonoscopy procedure.

7. The method of claim 1, wherein the water introduction comprises at least one period of continuous water introduction and at least one period of a pulsated water introduction, and wherein the analysis compares analyzing is configured to compare the sensed acoustic signals, which are sensed during the at least two periods.

8. A system comprising:
   a water delivery unit comprising a water supply and a nozzle connected thereto, configured to introduce water controllably into a large intestine of a patient,
   a drainage configured to drain, by gravity, the introduced water with contents of the patient's large intestine,
   a plurality of acoustic sensors that are attachable to an abdomen of the patient and are configured to sense acoustic signals at the patient's abdomen, and
   a processing unit configured to determine a large intestine cleanliness level of the patient's large intestine according to the drained contents of the patient's large intestine,
   wherein the processing unit is further connected to the acoustic sensors and configured to derive large intestine diagnostic characteristics of the patient's large intestine by analyzing and correlating the sensed acoustic signals received from the acoustic sensors with parameters of the drained water and contents,
   wherein the derived large intestine diagnostic characteristics provide gastrointestinal diagnosis of the patient.

* * * * *